(12) United States Patent
Winslow

(10) Patent No.: US 7,968,127 B2
(45) Date of Patent: Jun. 28, 2011

(54) REVERSE VITAMIN K EFFECT VIA PHOTODYNAMIC OXIDATION TARGETED AT VASCULAR ENDOTHELIUM, FIBRIN AND BLOOD PLATELETS

(76) Inventor: David E. Winslow, Highland Village, TX (US)

(*) Notice: Subject to any disclaimer, the term of this patent is extended or adjusted under 35 U.S.C. 154(b) by 595 days.

(21) Appl. No.: 12/180,872

(22) Filed: Jul. 28, 2008

(65) Prior Publication Data

US 2010/0021566 A1    Jan. 28, 2010

(51) Int. Cl.
*A61K 31/00* (2006.01)

(52) U.S. Cl. ............... 424/667; 424/133.1; 514/167; 514/7.8; 514/410; 514/681; 514/224.8; 514/411; 514/454

(58) Field of Classification Search .......... 424/667, 424/133.1; 514/167, 7.8, 410, 681, 224.8, 514/411, 454
See application file for complete search history.

(56) References Cited

U.S. PATENT DOCUMENTS

| | | | |
|---|---|---|---|
| 5,789,433 | A | 8/1998 | Chan et al. |
| 6,096,776 | A | 8/2000 | Chan et al. |
| 6,235,767 | B1 | 5/2001 | Kelly et al. |
| 6,790,463 | B2 | 9/2004 | Hofmann et al. |
| 2008/0069814 | A1* | 3/2008 | Curd et al. .......... 424/133.1 |

OTHER PUBLICATIONS

Michael Nesheim, PhD; "Thrombin and Fibrinolysis" (Chest. 2003;124:33S-39S.) © 2003 American College of Chest Physicians.
Bajzar L, Morser J, Nesheim J; TAFI, or plasma procarboxypeptidase B, couples the coagulation and fibrinolytic cascades through the thrombin-thrombomodulin complex.
Hofmann, Nadalo, Winslow; A Novel Intracellular Peroxidation-Inducing Drug Therapy for the Treatment of Post Cardiac Procedure Angina Pectoris and Cardiac Insufficiency.
Mansfield, Brown, McEwan; Photodynamic therapy: shedding light on restenosis; Heart 2001;86:612-618.
Su, Frederick; Photodynamic therapy: a maturing medical technology; Feb. 2000; No. 194.
Kereiakes; Coronary Artery Restenosis: Vision to the Future; Reviews in Cardiovascular Medicine; vol. 5, Suppl. 2 2004.
Mallat and Tedgui; Current Perspective on the Role of Apoptosis in Atherothrombotic Disease; Circulation Research; 2001;88:998-1003.
Kereiakes; Coronary Small-Vessel Stenting in the Era of Drug Elution; Reviews in Cardiovascular Medicine; S34 vol. 5 Suppl. 2 2004.
McClean; Stent Design: Implications for Restenosis; Reviews in Cardiovascular Medicine; S16 vol. 3 Suppl. 5 2002.
Kereiakes; Thrombosis and Drug-Eluting Stents: A Critical Appraisal; Reviews in Cardiovascular Medicine; vol. 5 No. 1 2004.
Sluijter, Smeets, Velema, Pasterkamp, De Kleijn; Increased collagen turnover is only partly associated with collagen fiber deposition in the arterial response to injury; Cardiovascular Research 61 (2004) 186-195.

Chandrasekharan, Simmons; The cyclooxygenases; Genome Biology 2004, 5:241.
Campbell; Drug-eluting Stents: Role of Stent Design, Delivery Vehicle, and Drug Selection; Reviews in Cardiovascular Medicine, S10 vol. 3 Suppl. 5 2002.
Editorial; Glyoxylide; htt://www.williamfkoch.com/texts/editorial/F.JAMERASSOC.htm(1 of 43)Jan. 5, 2005.
Costa, Lansky, Mintz, Mehran, Tsuchiya, Negoita, Gilutz, Nikolsky, Fahy, Pop, Cristea, Carlier, Dangas, Stone, Leon, Muller, Techen, and Grube; Angiographic Results of the First Human Experience with Everolimus-Eluting Stents for the Treatment of Coronary Lesions (the Future I Trial).
Rocnik, Chan, Pickering; Evidence for a Role of Collagen Synthesis in Arterial Smooth Muscle Cell Migration; J. Clin. Invest. vol. 101, No. 9, May 1998, 1889-1898.
Maruyama, Sekimoto, Ishibashi, Inouye, Oshima, Yamaguchi, and Abe; Suppression of neutrophil accumulation in mice by cutaneous application of geranium essential oil; Journal of Inflammation 2005, 2:1 doi:10.1186/1476-9255-2-1.
Spectroscopic Methods in Structure Determination.
Hulten, Holmstrom, and Soussi; Harmful Singlet Oxygen can be helpful; Free Radical Biology & Medicine, vol. 27, Nos. 11/12 pp, 1203-1207, 1999.
Nakamura, Lee, and Yeung; Identification and Treatment of Vulnerable Plaque; Coronary Artery Restenosis; S22 vol. 5 Suppl. 2 2004 Reviews in Cardiovascular Medicine.
Kereiakes, The Emperor's Clothes —In Search of the Vulnerable Plaque; Circulation —American Heart Association *Learn and Life*; Circulation. 2003; 107:2076.
Watson (reviewed); Shimada; Atherosclerosis; Reviews in Cardiovascular Medicine, vol. 5 No. 1 2004.
Holmes, Jr.; In-Stent Restenosis; Reviews in Cardiovascular Medicine, vol. 2 No. 3 2001.
Brinker; What Every Cardiologist Should Know About Intravascular Contrast; Reviews in Cardiovascular Medicine, vol. 4 Suppl. 5 2003.
Odinokov, Spivak, Emelyanova, Mallyabaeva, Nazarova, Dzhemilev; Synthesis of α-tocopherol (vitamin E), vitamin $K_1$-chromanol, and their analogs in the presence of aluminosilicate catalysts Tseokar-10 and Pentasil; ARKIVOC 2003(xiii) 101-118; ISSN 1424-6376.
Niki; Antioxidants and atherosclerosis; Biochemical Society Transactions (2004) vol. 32, part 1.
Irani; Oxidant Signaling in Vascular Cell Growth, Death, and Survival; 2000 American heart Association, Inc.
Burner, Krapfenbauer, Furtmuller, Regelsberger, Obinger; Oxidation of hydroquinone, 2,3-dimethylhydroquinone and 2,3,5-trimethylhydroquinone by human myeloperoxidase; Redox Report, vol. 5, No. 4, 2000.

(Continued)

*Primary Examiner* — Jean Witz
*Assistant Examiner* — Anna Falkowitz
(74) *Attorney, Agent, or Firm* — Barnes & Thornburg LLP

(57) ABSTRACT

A formulation or preparation for treating and preventing arterial and venous thrombi is provided. This preparation includes a non-metal containing photodynamic dye and a fat soluble vitamin. A method of administration for treatment and prophylaxis of arterial and venous thrombi is also provided. This method includes steps of: combining a non-metal containing photodynamic dye and a fat soluble vitamin; combining the non-metal containing photodynamic dye and fat soluble vitamin with a sodium solution; and administering the combination of non-metal containing photodynamic dye, fat soluble vitamin, and sodium solution as an intravenous drip.

28 Claims, No Drawings

OTHER PUBLICATIONS

Schwartz and Henry; Pathophysiology of Coronary Artery Restenosis; Reviews in Cardiovascular Medicine, vol. 3 Suppl. 5 2002.

Overhaus, Heckenkamp, Kossodo, Leszczynski, and Lamuraglia; Photodynamic Therapy Generates a Matrix Barrier to Invasive Vascular Cell Migration; 2000 American Heart Association, Inc.

Kereiakes, Szyniszewski, Wahr, Herrmann, Simon, Rogers, Kramer, Shear, Yeung, Shunk, Chou, Popma, Fitzgerald, Carroll, Forer, and Adelman; Phase I Drug and Light Dose-Escalation Trial of Motexafin Lutetium and Far Red Light Activation (Phototherapy) in Subjects With Coronary Artery Disease Undergoing Percutaneous Coronary Intervention and Stent Deployment; DOI: 10.1161/01.CIR.0000087602.91755.19.

Kipshidze and Sahota; Photoangioplasty Recount: Clear Punch or Dimpled Chad?

Rockson, Lorenz, Cheong, Woodburn; Photoangioplasty-An Emerging Clinical Cardiovascular Role for Photodynamic Therapy.

Wang, Gao, Zhou, and Selke; Nanomaterials and singlet oxygen photosensitizers: potential applications in photodynamic therapy; J. Mater. Chem., 2004, 14(4), 487-493 DOI: 10.1039/b311429e.

Mansfield, Bown, McEwan; Photodynamic therapy: shedding light on restenosis; Review —Heart 2001;86:612-618.

Shallenberger, 13 Major Effects of Ozone on the Human Body.

* cited by examiner

REVERSE VITAMIN K EFFECT VIA PHOTODYNAMIC OXIDATION TARGETED AT VASCULAR ENDOTHELIUM, FIBRIN AND BLOOD PLATELETS

TECHNICAL FIELD

The present disclosure relates to the formulation and administration of a compound for the treatment and prevention of existing thrombi and associated vascular related disease processes.

BACKGROUND AND SUMMARY

An embolus is an intravascular solid, liquid or gaseous mass that travels through the bloodstream to a site spaced apart from its origin. The majority of all solid emboli are derived from venous and arterial thrombi. Indeed, thrombosis and embolism are so closely interrelated they give rise to the term thromboembolism.

Infarcts are areas of ischemic necrosis of tissue. They are usually caused by thromboembolic occlusion of a vessel. Thromboembolic infarctions of the heart, lungs and brain collectively are believed to account for more deaths than all forms of cancer and infectious disease combined. Thromboembolism and infarction is further believed to constitute the dominating clinical problems today in all industrialized nations.

A variety of reactive oxygen species (ROS) have been shown to inhibit or inactivate thrombin and other serine proteases. Photodynamic dyes in biological systems can generate the ROS which specifically targets the vascular endothelium mimicking naturally occurring redox reactions. This results in targeted stimulation of the fibrinolytic system (i.e., lysis of existing thrombi). The inactivation of specific blood clotting factors along with the resultant physiologic response to the specifically targeted ROS, leads to an overall systemic anticoagulation state which prevents future thrombus formation.

Present anticoagulant therapies used for inhibition of thrombi formation such as heparins and coumarins, have a number of untoward and sometimes unexpected effects. Discovery of the human Thrombin-activatable fibrinolysis inhibitor (TAFI) anifibrinolytic system has provided strong evidence that while the use of these anticoagulants may effectively prevent the formation of future thrombi, they can paradoxically discourage fibrinolysis of existing thrombi. The result is a net addition of fibrin to existing thrombi. Similarly, tissue plasminogen activator (tPA) used to lyse existing thrombi is fraught with life threatening side effects. This therapy also has a narrow therapeutic window—less than three hours following thrombus formation. There is, thus, a need for new formulations having anticoagulant activity which does not favor growth of existing thrombi and is safer and more therapeutically flexible.

An illustrative embodiment of the present disclosure provides a preparation for treating arterial and venous thrombi. This preparation comprises a non-metal containing photodynamic dye and a fat soluble vitamin. In a further illustrative embodiment, the vitamin is vitamin K, despite being known for assisting blood clotting.

Indeed, it is known in the art that certain proteins that participate in the blood clotting cascade are vitamin K dependent. Obviously this is a double-edged sword. In the context of wound clotting, vitamin K can be beneficial. In the context of pathologic blood clotting or thrombus formation within an artery or vein, however, vitamin K can be problematic. It is therefore, believed, that vitamin K would not be an obvious choice in the field of anticoagulant pharmaceuticals In medicine, vitamin K is used to promote the clotting of blood. In human physiology, vitamin K is essential in order for the blood clotting cascade to function properly and therefore for blood to have the capability of clotting. The subject matter of the present disclosure employs vitamin K to create the opposite effect. When the formulation of the current invention is compounded in the particular order, the hydrocarbon side chain of vitamin K is cleaved from the mother quinone base of the vitamin K derivative.

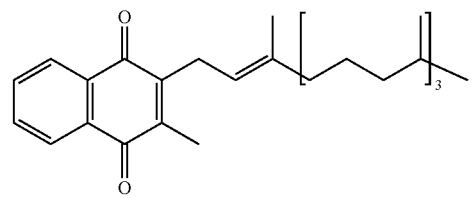

This is believed accomplished by mixing vitamin K with Geraniol Tetroxane. When this combination is then mixed with verteporfin, it is believed that the operative porphyrin-quinone complex is generated. It is this complex that is able to produce the necessary reactive oxygen species at specifically targeted sites in a 'cyclic manner' which produces said effects, not the vitamin K. If the formulation is not mixed in the proper order, it is believed that vitamin K will maintain its original structure and be available to make its usual contribution as the major promoter of blood clotting. In any event, adding vitamin K in any way shape or form to a compound designed to prevent blood clotting or designed to destroy existing blood clots would be counter-intuitive.

In the above and alternative embodiments, the preparation may also include: a photodynamic dye selected from a group consisting of a tricarbocyanine dye, tetramethylthionine chloride dye, a xanthene dye, and a benzo-porphyrin derivative (BPD) such as verteporfin, one of the fat soluble vitamins being vitamin A, D, E and K; the fat soluble vitamin being vitamin K; the photodynamic dyes being selected from a group consisting of methylene blue, indocyanine green, rose bengal, and verteporfin; verteporfin being combined together with the fat soluble vitamin; this combination being combined with a sodium salt; the sodium salt being sodium iodide; this combination being mixed into a physiologic carrier solution containing a metallic additive selected from the group consisting of gold, silver, copper, manganese and magnesium; and a readily available electron donor compatible with mammalian blood.

Another illustrative embodiment of the present disclosure provides a preparation for treating and preventing arterial and venous thrombi. This preparation's formulation comprises a fat soluble vitamin combined with a first solvent; this combination is then diluted with a second solvent; a first non-metal containing photodynamic dye is then chemically attached to the functional quinone group of the fat soluble vitamin in this mixture; one to three other non-metal containing photodynamic dyes are added to this mixture; a sodium salt is added to this mixture; and finally a second portion of the first solvent is added to this mixture.

In the above and alternative embodiments, the preparation may also include: the fat soluble vitamin being about 0.01 wt % vitamin K; the first solvent being about 20 wt % geraniol tetroxane in DMSO; the second solvent being about 99% DMSO; the first non-metal containing photodynamic dye is about 0.01 wt % verteporfin; and the second non-metal containing photodynamic dye is about 0.0088 wt % methylene blue; (sodium iodide solution can be substituted for IC Green) a third non-metal containing photodynamic dye being about 0.0574 wt % rose bengal; the first solvent comprising dimethyl sulfoxide and carboxylic acid derivatives; the second solvent comprising dimethyl sulfoxide; the second non-metal containing photodynamic dye being selected from a group consisting of verteporfin, indocyanine green, methylene blue and rose bengal; and a sodium solution or sodium salt, such as sodium iodide in a liquid form combined with the first portion of the second solvent combined with the first non-metal containing photodynamic dye, fat soluble vitamin, and first solvent combined with the second portion of the second solvent combined with the second non-metal containing photodynamic dye.

Yet another illustrative embodiment of the present disclosure provides a method of administration for treatment and prophylaxis of arterial and venous thrombi. This illustrative method comprises the steps of: combining a non-metal containing photodynamic dye and a fat soluble vitamin; combining the non-metal containing photodynamic dye and fat soluble vitamin with a sodium solution, such as about 0.9% sodium chloride (NaCl) and administering the combination of non-metal containing photodynamic dye, fat soluble vitamin, and sodium solution as an intravenous drip.

In the above and alternative embodiments, the method may also include one or more of the following steps: administering the intravenous drip for about 10 to 60 minutes; repeating the administration of the intravenous drip on a daily basis as needed for up to about eight days; combining a non-metal containing photodynamic dye that is selected from a group consisting of a tricarbocyanine dye, tetramethylthionine chloride dye, a xanthene dye and a benzo-porphyrin derivative dye; combining the fat soluble vitamin that is selected from a group consisting of vitamin A, vitamin D, vitamin E and vitamin K; combining the photodynamic dye that is selected from a group consisting of verteporfin, methylene blue, indocyanine green and rose bengal; combining the non-metal containing photodynamic dye and fat soluble vitamin with a sodium salt solution, such as sodium iodide; combining the non-metal containing photodynamic dye, fat soluble vitamin and salt solution such as with a sodium chloride metallic additive; and combining the non-metal containing photodynamic dye, fat soluble vitamin and salt solution with the metallic additive that is selected from a group consisting of gold, silver, copper, manganese and magnesium; vitamin K being added to a first solvent—Geraniol Tetroxane in DMSO, this being added to a second solvent—99% DMSO, this being added to verteporfin, this being diluted into more of the second solvent, sodium iodide being added, Methylene Blue being added, rose bengal being added, this being added to a physiologic carrier solution such as about 0.9% Sodium Chloride containing a metallic additive that is selected from the group consisting of gold, silver, copper, manganese and magnesium and an electron donor that is compatible with mammalian blood such as Vitamin C.

Further embodiments of the present disclosure provide compounds containing regioisomers of one or more of the following in combination with a fat-soluble vitamin, a non-metal containing benzoporphyrin derivative (BPD) photodynamic dye, and/or a synthetic tricarbocyanine photodynamic dye, and/or a tetramethylthionine chloride dye, and/or a xanthene dye for the treatment and prevention of thrombi and thrombus formation and other vascular related disease processes.

Still further embodiments of the present disclosure provide compounds containing regioisomers of one or more of the following in combination with a synthetic fat-soluble vitamin, a synthetic non-metal containing BPD photodynamic dye, a synthetic tricarbocyanine photodynamic dye, a synthetic tetramethylthionine chloride dye, or a xanthene dye for treatment and prevention of thrombi and thrombus formation and other vascular related disease processes.

Additional features and advantages of the formulation, preparation, and administration of the compound will become apparent to those skilled in the art upon consideration of the following detailed descriptions exemplifying the best mode of carrying out the formulation, preparation, and administration of the compound as presently perceived.

DESCRIPTION OF ILLUSTRATIVE EMBODIMENTS

An embodiment of the present disclosure is a composition that includes a non-metal containing photodynamic BPD dye such as verteporfin and a fat soluable vitamin. In addition, or in the alternative, embodiments may include, tricarbocyanine dye (indocyanine green), sodium iodide, tetramethylthionine chloride dye (methylene blue) and/or xanthene dye (rose bengal). The fat soluble vitamin for the composition may be vitamin K1.

Although this disclosure is not intended to be bound to any theory, it is believed that the photoactive substance simulates (at specifically targeted sites) the many biological energy transductions which occur naturally during oxidative phosphorylation in mitochondria. As postulated by chemiosmotic theory, a proton-motive force, or conservation of part of the energy of oxidation results from the energy transductions which produce ATP. This can be written as:

$$ADP+Pi+\{H_+\}_{out} \leftarrow\, \cdot\, \cdot\, \cdot\, \rightarrow ATP+H_2O+\{H_+\}_{in}$$

The conserved energy appears to be interconvertible with the energy of chemical bonds. This conserved energy maintains the flow of electrons necessary to carry out all the biological red ox reactions to prevent chemical stagnation of the biological system as a whole. Of particular interest is the targeted simulation of naturally occurring red ox reactions. It is postulated that with the resultant cyclic creation of proton-motive force and through energy transductions made locally available for the conversion of ADP→ATP, a local deterrent to blood platelet aggregation and accumulation is created via rapid local depletion of ADP. Otherwise, ADP naturally increases at the specific target site secondary to inflammatory condition(s) results in platelet aggregation and accumulation. It is further postulated that through the specifically targeted local creation of a pro-oxidative milieu via the compound of the present disclosure, there occurs a local flip in the negatively charged vascular endothelium and the positively charged blood platelet electro-repulsive state (the natural anti-thrombotic state) to a locally positively charged vascular endothelium and negatively charged blood platelet electro-repulsive state (a likewise but opposite anti-thrombotic state).

Integrins are large binary protein complexes made up of two different types of polypeptide chains (called the alpha and beta subunits) that come together to form a "heterodimer" that is expressed on the surface of a cell. A large portion of the protein is extracellular (outside of the cell), and just a tiny tail of a few dozen amino acids protrudes through the membrane on the inside of the cell. The large extracellular portions are the domains that bind to molecules on the outside of the cells and mediate the interactions of the cell with other cells. Integrins are mediators of a host of normal and abnormal biological processes. They are important for inflammation, essential for platelet aggregation after vascular injury, and involved in cell motility. As such, they are involved in diseases where the normal mechanisms of platelet aggregation go awry—as in heart attacks, strokes, and other thrombotic events. They are also implicated in cancer metastasis. For instance, one of the molecules to which integrins bind is fibrinogen, a circulating dimeric protein that is present in large amounts in the blood which can bind integrins at both ends. This interaction is essential for mediating the aggregation of platelets. Platelets are covered with integrins (typically about 80,000 are on the surface of any given platelet). But the integrins need to be activated to bind fibrinogen. When they are not active, the platelets flow in the blood without sticking to each other or to blood vessel walls. An injury will cause the integrins to become activated. The activated integrins then bind to fibrinogen, which then bind to other activated integrins on other platelets, cross-linking many platelets into a massive thrombus.

The final step in the activation of integrins has shown to be the binding of talin. When talin binds to a beta subunit of β-integrin, it causes a conformational change in the integrin which is propagated across the membrane, changing the structures of the integrin domains extracellularly. Cysteine residue scanning of β-integrin, suggests "electrostatic steering" as a primary mechanism for effective platelet to endothelium and platelet to platelet adhesion. At the intracellular level, it is postulated that the pharmaceutical formulation of the current invention prevents talin to β-integrin binding via oxidative conformational changes in, pp $125^{FAK}$ (via Tyrosine protein kinase and tyrosyl radical formation.)

Using fibronectin and the Jurkat T-cell line as a prototype model, demonstrates that fibronectin stimulates tyrosine phosphorylation of p$125^{FAK}$ and that cross-linking of β1-integrins by insoluble fibronectin results in a p$125^{FAK}$/Zap 70 complex and in the induction of tyrosine phosphorylation. Disruption of this process via the formulation disclosed herein is believed to decrease WBC adhesion to fibrin and endothelial cells thereby altering (decreasing) the inflammatory process locally. These conformational perturbations have been elucidated through Cysteine residue scanning of β-integrin (transmembrane adhesion talin binding proteins) as sited above. With this disruption, the extracellular portion of the β-integrin binding sites is altered beyond recognition (e.g., not recognized by extracellular platelet integrins) as a binding site.

It is believed that the RGD (Arg-Gly-Asp) sequence is integral in the binding of extracellular surface integrins of platelets to vascular endothelium, collagen, prothrombin and heparin. It is, therefore, further believed that only minor changes to the extracellular portions of transmembrane integrins will lead to lack of their recognition by the RGD sequence. The platelet to platelet, platelet to endothelium and/or platelet to fibrin binding capacity are believed to be inhibited by the formulations of the present disclosure favoring anticoagulation and or normalization of blood flow.

In mitochondria, it is believed that H atoms removed from substrates are donated to the respiratory chain (porphyrins) and transferred to molecular oxygen forming the ROS superoxide. Through the action of superoxide dismutase (SOD) and then catalase, superoxide degenerates to hydrogen peroxide and then molecular oxygen and water with resultant energy production. Proton-motive force allows for this chain of events to occur even in the absence of an oxidizable substrate. It is further believed that the formulation of the present disclosure likewise locally allows for these specifically targeted transductions of energy and resultant transformations in relevant enzyme systems even in the absence of an oxidizable substrate thereby contributing to local fibrinolysis and the overall antithrombotic state thereby locally achieved.

Porphyrin generated ROS via the dark effects of verteporfin are specifically targeted to an existing thrombus via parenteral administration of the present formulation. The majority of these ROSs are believed to be superoxide. The chemical structure of an embodiment of the formulation incorporates the functional quinone group of vitamin K as a side chain of verteporfin. It is believed this porphyrin-quinone complex produces desired effects at specifically targeted sites in a cyclic manner.

Vitamin K is labile to oxidation and responsible for the activation and/or synthesis of plasma clotting factors VII, IX and X in the liver. The compositions of the present disclosure depletes vitamin K and thereby depletes vitamin K dependent plasma clotting factors in the liver and thereby at specifically targeted sites. The functional quinone group of vitamin K is incorporated as a side chain of verteporfin. When the constituents are mixed in the correct order, the functional quinone group portion of vitamin K is borrowed to chemically bond to verteporfin. The hydrocarbon chain (tail) of vitamin K is cleaved off. Accordingly, vitamin K is being used as a building block for the more important molecule, the porphyrin-quinone complex. This molecule is capable of performing redox reactions in a cyclic manner. The "reverse vitamin K effect" refers to the final outcome of the lysis and prevention of clots. It is not meant to imply that vitamin K is itself doing the opposite of what it normally does. The results are believed accomplished by the combined effects of the ROS generated at specifically targeted sites. The formulations of this disclosure may abolish and or normalize the sequleae of existing thrombi, possibly for up to about eight months following their formation, while simultaneously preventing the formation of future thrombi.

An illustrative manufacturing process for one of the formulations is as follows: adding about 20 mg. of vitamin K (10 mg/ml) to about two ml. of a solvent containing about 80% dimethylsulfoxide (DMSO) and about 20% carboxylic acid derivatives; diluting resulting composition in about 100 mls 99% DMSO; dissolving 15 mg. of verteporfin (lipholized cake) into the composition; separately adding about 25 mg. of indocyanine green (lypholized cake) and/or about 10 mg methylene blue (10 mg/ml.) into that solution; then combining 65 mg of rose bengal powder into that solution; and finally adding 14 more mls. of 80% DMSO and about 20% Geraniol Tetroxane (carboxylic acid derivatives) to that solution; resulting in about 119 mls. of the subject formulation. Another illustrative formulation is as follows:

DMSO=100 mls.=110,000 mg.=97.0617%(80%-99%)

Geraniol Tetroxane=16 mls.=3200 mg.=2.8236% (0.0002%-20%)

Vitamin K=2 mls.=20 mg.=0.0176%(0.0001%-1%)

Verteporfin=15 mg.=0.0132%(0.0001-1%)

Methylene Blue=1 ml.=10 mg.=0.0088%(0.00001-1%)

Sodium Iodide=0.4 ml.=20 mg.=0.0176%(0.0001-1%)

Rose Bengal=65 mg=0.0574%(0.0005-1%)

It can be appreciated that if IC Green is used, sodium iodide can be omitted and visa versa. Other dyes that could be used are other natural or synthetic porphyrins, chlorophyllins, hemins, porphins, corrins, texaphrins, hematoxylin, eosin, erythrosine, flavinoids, lactoflavin, anthracene dyes, hypericin, methylcholanthrene, neutral red and flourescein. It is also appreciated that the quantities and percentages can vary.

A method of administration for treatment and prophylaxis of arterial and venous thrombi using the previously illustrated preparation comprises: combining about one cc of sodium ascorbate (500 mg/ml) to 100 cc. of 0.9 NaCl; adding about one half (0.5) cc of the subject formulation; administering as an IV drip to the patient for ten to sixty minutes; repeating on a daily basis as needed for up to eight days. Prophylaxis of future thrombus formation is achieved by administration of about two cc of the subject formulation about every three to four months. It is also believed that other related vascular disease states can be treated by administration of the subject formulation.

It is believed that formulations of the present disclosure targets one or more of the following conditions: vascular endothelium and areas of vascular endothelial injury, thereby negatively effecting the aggregation of blood platelets in areas of vascular endothelial injury; fibrin of existing arterial and venous thrombi, thereby negatively effecting the aggregation of blood platelets and the net addition of fibrin to, and within, arterial and venous thrombi; fibrin in mural thrombi within the heart chambers, thereby preventing atrial fibrillation induced micro-thrombi within the atrial heart chambers; fibrin within thrombi formed in the low blood flow area of an arterial aneurysm, thereby preventing arterial thromboembolism; bone marrow resulting in normalization of bone marrow derived blood forming elements thereby increasing immune function; macrophage foam cells within atheromatous plaque; atheromatous plaque within coronary arteries; atheromatous plaque within carotid arteries; atheromatous plaque within cerebral arteries; atheromatous plaque within renal arteries; atheromatous plaque within peripheral arteries; neovascular endothelium and drusen within retinal arteries; collagen and vascular smooth muscle constituents within occluded and partially occluded man made arterial stenting devices, man made venous stenting devices, human vein to artery bypass graft anastomoses and human artery to artery bypass graft anastomoses thereby increasing blood flow within these devices and anastomoses; vascular endothelium within varicose veins; vascular endothelium within superficial veins.

It is further believed that the formulations of the present disclosure promote one or more of the following: debulking of atheromatous arterial plaque and retinal arteriolar drusen and extravasation of cholesterol within arterial walls, resulting in increased blood flow and thereby improving cardiac function, brain function, kidney function and skeletal muscle function while reducing symptoms of angina in coronary artery disease, transient ischemic attack in carotid artery occlusive disease, senile dementia in cerebral artery occlusive disease, hypertension in renal artery occlusive disease, claudication in peripheral artery occlusive disease and decreased visual acuity in the dry form of age related macular degeneration; stabilization of atheromatous arterial plaque resulting in decreased risk of myocardial infarction, transient ischemic attack and cerebrovascular accident; treatment and prevention of Thrombotic Thrombocytopenic Purpura (TTP); treatment and prevention of Dissiminated Intervascular Coagulopathy (DIC); treatment and prevention of phlebitis; treatment and prevention of congestive heart failure (CHF); treatment and prevention of pulmonary embolism (PE); treatment and prevention of cardiac arrhythmias; treatment of peripheral neuropathies and peripheral venous stasis ulceration associated with diabetes mellitus; treatment of rheumatoid arthritis and a variety of other auto-immune diseases and disorders; treatment of Type IV delayed hypersensitivity reactions such as delayed drug reactions; treatment of anemias; treatment of chronic pain; treatment of chronic fatigue and fibromyalgia; and treatment of infectious diseases.

It is even further believed that the formulations of the present disclosure can have an effect on one or more of the following: minimizing varicose veins; obliterating of spider nevi, vascular purpura and the lesions which represent the epidermal changes of chronic lower extremity edema and upper extremity micro-vascular fragility; normalizing blood lipid constituents; balancing endogenous hormone production thereby normalizing endocrine function; and increasing spermatozoa count thereby increasing male fertility.

The disclosure is further illustrated but is not intended to be limited by the following examples.

Example 1

A 65 year old female suffered a fall which inflicted trauma to the left lower extremity above the knee. There was diffuse edema present and the patient was experiencing extreme pain. Ambulation was difficult. A venous angiodynagram duplex scan of the left lower extremity revealed noncompressability with acute thrombus formation in the common femoral, superficial femoral and popliteal veins. The patient was hospitalized and anticoagulated with heparin over the following two weeks. She was sent home on coumadin and anti-inflammatory medication. The left lower extremity continued to be diffusely swollen. The patient required 10 mg. of hydrocodone four times per day to deal with the pain in the left lower extremity. The patient was non-ambulatory for all practical purposes. Over the next three to four weeks there was no improvement in the patient's condition. The patient was given an intravenous infusion of 0.5 cc of the subject formulation in 100 cc 0.9% NaCl and 1 cc of sodium ascorbate (500 mg/ml). She described immediate relief of pain. Ambulation was improved to near normal within the first 24 hours following the intravenous infusion. The patient no longer required pain medication. All symptoms of swelling disappeared in the week following the intravenous infusion. Infusion was repeated two months later as a precautionary and preventative measure.

Example 2

Three days following endoscopic "cleaning up" of the left knee joint with repair of the medial collateral ligament, a 53 year old male developed painful swelling and erythema in the left calf while keeping his left lower extremity elevated following the surgery. Venous Angiodynagram revealed a large thrombus in the left politeal vein. The patient refused hospitalization. One week later the patient was given an intravenous infusion of 1 cc of the subject formulation in 100 cc 0.9% NaCl and 1 cc of sodium ascorbate (500 mg/ml). There was some immediate relief of pain following the intravenous infusion. The following day an infusion of 2 cc of the subject formulation was administered in the same manner. All symptoms of pain and swelling in the calf disappeared on the day of the second intravenous infusion. A repeat Angiodynagram the following week revealed dissolution of the thrombus.

Example 3

A 74 year old male suffered from swelling behind his right knee. He had a known Baker's cyst but also noticed some recent enlargement behind the right knee and the area was more painful than usual. There was also increase in temperature to touch in the area. Arterial Angiodynagram of the right lower extremity revealed an aneurysm of the popliteal artery, 8-10 cm in length and 4-5 cm in width. There were multiple thrombi within the low pressure, low flow area of the aneurysm. There also appeared to be a pseudoaneurysm superimposed over an area of the true aneurysm. The patient was given a total of 3 ccs of the subject formulation over three weeks by intravenous infusion. Pain was reduced in the area behind the patient's knee and the knee joint became more mobile with less apparent inflammation following the initial treatment. Repeat arterial Angiodynagram three weeks later revealed complete resolution of the arterial thrombi within the aneurysm. The arterial Angiodynagram was repeated approximately one year later and although the aneurysm had grown approximately 2-3 cm in length, there were still no significant thrombi present within the aneurysm. The patient currently receives a total of 2 ccs of the formulation of the current invention every three to four months for prevention of thrombus formation.

Example 4

A 57 year old male with severe varicose veins in both lower extremities presented with a popliteal deep venous thrombosis in the right lower extremity three days post arthroscopic knee surgery. He had a history of deep venous thrombosis and had previously had multiple varicosities tied off in the right lower extremity to prevent thromboembolism. He was anticoagulated. Eight months later he was still taking 6 mgs. of Coumadin daily and still had pain and swelling in the area of the DVT. He was also experiencing pain in both lower extremities due to muscle cramps and described generalized weakness in both lower extremities. The patient was given a total of 1 cc. of the subject formulation over three days. Following the second 0.25 cc. administration on day two of treatment, the pain and swelling in the area of the DVT completely resolved. The "knot" where the DVT had been was no longer palpable. Over several days following the third administration, the patient was no longer experiencing cramping in his lower extremities and he stated that both of his legs were feeling stronger. A repeat Angiodynagram was ordered three weeks later which showed dissolution and resolution of the patient's thrombus.

Although the present disclosure has been described with reference to particular means, materials and embodiments, from the foregoing description, one skilled in the art can easily ascertain the essential characteristics of the present disclosure and various changes and modifications may be made to adapt the various uses and characteristics without departing from the spirit and scope of the present invention as set forth in the following claims.

What is claimed:

1. A preparation for treating arterial and venous thrombi comprising: a photodynamic dye; and fat soluble vitamin K.

2. The preparation of claim 1, wherein the photodynamic dye is selected from a group consisting of a benzoporphyrin derivative (BPD) dye, tricarbocyanine dye, tetramethylthionine chloride dye and a xanthene dye.

3. The preparation of claim 1, wherein the photodynamic dye is selected from a group consisting of a verteporfin, methylene blue, indocyanine green and rose bengal.

4. The preparation of claim 1, wherein the non-metal containing photodynamic dye and the fat soluble vitamin are combined with a sodium solution.

5. The preparation of claim 1, wherein the non-metal containing photodynamic dye and the fat soluble vitamin are combined with a sodium chloride solution.

6. The preparation of claim 1, further comprising a metallic additive.

7. The preparation of claim 6, wherein the metallic additive is selected from a group consisting of gold, silver, copper, manganese and magnesium.

8. The preparation of claim 1, further comprising a physiologic carrier solution containing a readily available electron donor compatible with mammalian blood.

9. A preparation for treating arterial and venous thrombi comprising the following formulation: fat soluble vitamin K combined with a first solvent;
a first non-metal containing photodynamic dye combined with fat soluble vitamin K combined with the first solvent; a second solvent;
wherein a first portion of the second solvent is combined with the first non-metal containing photodynamic dye, fat soluble vitamin K, and first solvent;
a second non-metal containing photodynamic dye;
wherein a second portion of the second solvent is combined with the second non-metal containing photodynamic dye, and wherein the first portion of the second solvent combined with the first non-metal containing photodynamic dye, fat soluble vitamin K, and first solvent is combined with the second portion of the second solvent combined with the second non-metal containing photodynamic dye.

10. The preparation of claim 9, wherein the formulation further comprises fat soluble vitamin is about 0.0176 wt % vitamin K; the first solvent is about 20 wt % geraniol tetroxane in DMSO; the second solvent is about 99% DMSO; the first non-metal containing photodynamic dye is about 0.0132 wt % verteporfin; and the second non-metal containing photodynamic dye is <5 wt % sodium iodide of IC Green if IC Green is used or 0.0176 wt % sodium iodide if sodium iodide replaces IC Green.

11. The preparation of claim 10, further comprising a third non-metal containing photodynamic dye being about 0.0574 wt % rose bengal.

12. The preparation of claim 9, wherein the first non-metal containing photodynamic dye is verteporfin.

13. The preparation of claim 9, wherein the first solvent comprises dimethyl sulfoxide and carboxylic acid derivatives.

14. The preparation of claim 9, wherein the second solvent comprises DMSO.

15. The preparation of claim 9, wherein the second non-metal containing photodynamic dye is selected from a group consisting of verteporfin, indocyanine green, and methylene blue.

16. The preparation of claim 9, further comprising a sodium solution that is combined with the first portion of the second solvent combined with the first non-metal containing photodynamic dye, fat soluble vitamin K, and first solvent combined with the second portion of the second solvent combined with the second non-metal containing photodynamic dye.

17. The preparation of claim 10, further comprising about 0.0132% benzoporphyrin derivative.

18. The preparation of claim 10, further comprising a third solvent of about 2.8236 wt % geraniol tetroxane in DMSO.

19. A method of administration for treatment and prophylaxis of arterial and venous thrombi comprising:
   a) combining a non-metal containing photodynamic dye and fat soluble vitamin K;
   b) combining the non-metal containing photodynamic dye and fat soluble vitamin K with a sodium solution; and
   c) administering the combination of non-metal containing photodynamic dye, fat soluble vitamin K, and sodium solution as an intravenous drip.

20. The method of claim 19, further comprising the step of administering the intravenous drip for about 10 to 60 minutes.

21. The method of claim 20, further comprising the step of repeating the administration of the intravenous drip on a daily basis for up to eight days.

22. The method of claim 19, further comprising the step of combining a non-metal containing photodynamic dye that is selected from a group consisting of a tricarbocyanine dye, tetramethylthionine chloride dye and a xanthene dye.

23. The method of claim 19, further comprising the step of combining the photodynamic dye that is selected from a group consisting of a verteporfin, methylene blue and indocyanine green/sodium iodide and rose bengal.

24. The method of claim 19, further comprising the step of combining the non-metal containing photodynamic dye and the fat soluble vitamin K with the sodium solution that is a sodium chloride solution.

25. The method of claim 19, further comprising the step of combining the non-metal containing photodynamic dye, fat soluble vitamin K, sodium solution with a metallic additive.

26. The method of claim 19, further comprising the step of combining the non-metal containing photodynamic dye, fat soluble vitamin K, sodium solution with the metallic additive that is selected from a group consisting of gold, silver, copper, manganese and magnesium.

27. A preparation of treating arterial and venous thrombi comprising:
   about 0.0176 weight percent vitamin K, about 0.0088 weight percent methylene blue, about 0.0176 weight percent sodium iodide, about 0.0574 weight percent rose bengal, and the balance being an intravenous solution.

28. The preparation of treating arterial and venous thrombi of claim 27, wherein the intravenous solution further comprises about 2.8236 weight percent geraniol tetroxane in DMSO, about 97.0617 weight percent DMSO, and about 0.0132 weight percent benzoporphyrin derivative.

* * * * *